(12) United States Patent
Kühnel

(10) Patent No.: US 10,716,697 B2
(45) Date of Patent: Jul. 21, 2020

(54) APPLICATION DEVICE FOR NASAL SPLINTS

(71) Applicant: S-F-X-Holding GmbH, Freiburg (DE)

(72) Inventor: Thomas Kühnel, Regensburg (DE)

(73) Assignee: S-F-X-Holding GmbH, Freiburg (DE)

( * ) Notice: Subject to any disclaimer, the term of this patent is extended or adjusted under 35 U.S.C. 154(b) by 629 days.

(21) Appl. No.: 15/072,609

(22) Filed: Mar. 17, 2016

(65) Prior Publication Data

US 2016/0270946 A1 Sep. 22, 2016

(30) Foreign Application Priority Data

Mar. 20, 2015 (DE) .................. 10 2015 104 243

(51) Int. Cl.
*A61F 5/08* (2006.01)
(52) U.S. Cl.
CPC ..................... *A61F 5/08* (2013.01)
(58) Field of Classification Search
CPC A61F 5/08; A61B 2017/0409; A61B 17/0401
USPC .................................................. 606/204.45
See application file for complete search history.

(56) References Cited

U.S. PATENT DOCUMENTS

| 4,402,314 | A | 9/1983 | Goode | |
|---|---|---|---|---|
| 6,186,965 | B1 | 2/2001 | Patterson | |
| 2004/0138682 | A1* | 7/2004 | Onuki | A61B 17/0401 606/144 |
| 2008/0142018 | A1* | 6/2008 | Doshi | A61F 5/08 128/207.18 |
| 2012/0271209 | A1 | 10/2012 | Mobley | |
| 2013/0338700 | A1* | 12/2013 | Matheny | A61F 5/08 606/199 |
| 2015/0250470 | A1* | 9/2015 | Vargas | A61B 17/0401 606/232 |

OTHER PUBLICATIONS

Chinchilla Friends Forum, Chinchilla General Nutrition, "Feeding recovery food—this is how it works", dated Nov. 19, 2007; http://www.chinchilla-freunde.de/forum/wbb3/wbb/board1-chinchilla-allgemein/board18-emährung/1579-breimährung-so-geht-s-richtig/.

* cited by examiner

*Primary Examiner* — Diane D Yabut
*Assistant Examiner* — Majid Jamialahmadi
(74) *Attorney, Agent, or Firm* — Budzyn IP Law, LLC

(57) ABSTRACT

In accordance with invention an application device for nasal splints is created, comprising at least one hollow body for accommodating a nasal splint, and a plunger which can be moved within the hollow body, wherein one end face of the hollow body is open so that a nasal splint contained in the hollow body can be introduced through a movement of the plunger from the hollow body through the open end face into the nose of a patient.

13 Claims, 9 Drawing Sheets

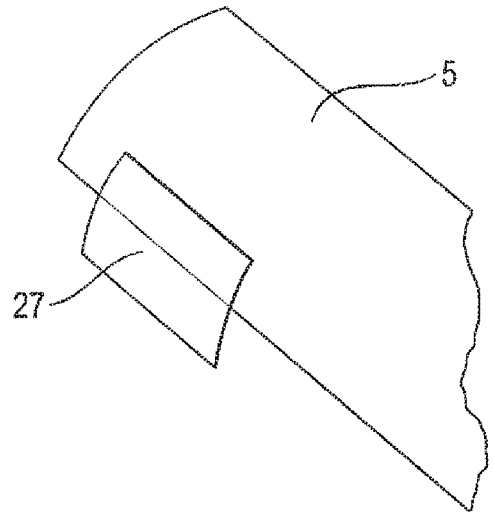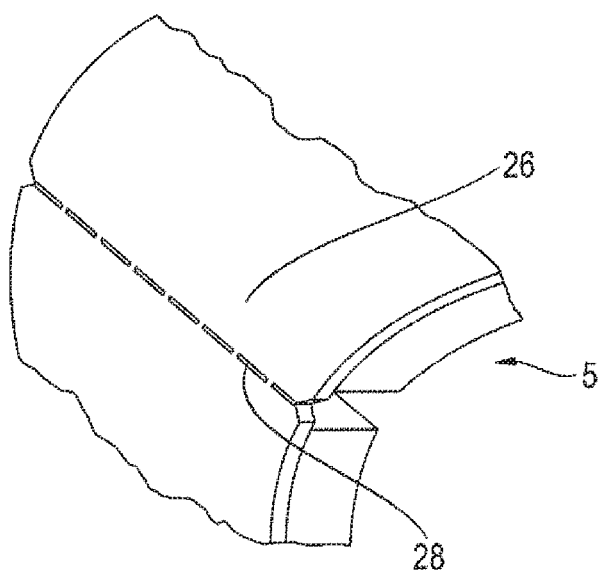

APPLICATION DEVICE FOR NASAL SPLINTS

The invention relates to an application device for nasal splints as well as a nasal splint.

Nasal splints are used for the postoperative stabilisation and splinting of the nasal septum. Here, after an operation the nasal septum is splinted by way of two plastic plates (nasal splints) in order to assure straight growing together of the nasal septum, a splint to provide epithelialisation of mucous membrane wounds and to prevent blood effusion. For this the splints are fixed to the nasal septum through sutures or tamponades. A disadvantage of this is that too tight a suture can lead to pressure necrosis, while too slack a suture does not adequately fix the nasal splints.

It is known to provide nasal splints with magnets so that two opposite nasal splints applied to the nasal septum attract each other magnetically and become fixed to the nasal septum. Such nasal splints are known from U.S. Pat. No. 4,402,314. Here too there is the problem that too strong magnetic forces can lead to necrosis, where too week a magnetic force may not be sufficient to adequately fix the nasal splints in place.

Conventionally such nasal splints are introduced into the nostrils of a patient by means of tweezer-like applicators. In order to allow problem-free introduction of the splints their size is orientated to the size of the patient's nostrils. However, this can result in the surface area of the nasal splint being too small in relation to the surface area of the nasal septum.

The objective is to eliminate or reduce this problem.

This task is solved by the invention set out in claim 1. Advantageous embodiments can be found in the sub-claims. A further aspect of the present invention is set out in the sub-claims.

In accordance with the invention an application device for nasal splints is created, comprising at least one hollow body for accommodating a nasal splint and a plunger which can be moved in the hollow body, wherein one end face of the hollow body is open so that through a movement of the plunger a nasal splint contained in the hollow body can be introduced from the hollow body through the open end face into the nose of a patient.

By means of the application device in accordance with the invention nasal splints can be simply introduced into a patient's nose. For this a nasal splint is first of all accommodated in the hollow body of the application device in a folded together or rolled up state. The application device is then inserted with the end opening into the nose of the patient. Thereafter the plunger in the hollow body is moved in the direction of the patient so that the nasal splint is pushed out by the plunger. Hereupon the nasal splint unfolds and attaches itself to the nasal septum of the patient.

By means of the application device in accordance with the invention nasal splints with a surface area larger than conventional nasal splints can be inserted into the nose of a patient. The nasal splints can be held in the application device in a rolled-up or folded together state and introduced into the nose. As the nasal splints are not yet unfolded or unrolled during the introduction process their size is not restricted by the size of the nostril. In all events the introduction process is more pleasant for the patient and the risk of injury to the nasal opening is reduced.

Advantageously this not only provides the possibility of introducing larger nasal splint into the nose of a patient. Rather, it also allows nasal splints of a sufficient standard size to be used, whereby the standard size can be orientated to the size of the nasal septum of an average patient, irrespective of the size of the nostrils.

A further advantage of the present invention consists in the fact that the application device is simple to manufacture. In principle it is also possible to produce the application device through providing a conventional plastic syringe, the cylindrical hollow body of which is cut or sawn off, so that the end face on the side of the syringe facing the patient is open. Through this opening a folded together or rolled up nasal splint can be inserted into the hollow body and then introduced into the nose of a patient. In other words, the hollow body of the application device corresponds to the main body of a syringe, but without the tapering projection with the needle.

In an advantageous embodiment the at least one hollow body has a non-rounded cross-section, more particularly a cross-section with an essentially straight first side and an opposite rounded second side. Preferably the cross-section of the hollow body is adapted to the cross-section of the nostril of an average patient whereby the introduction of the application device into the patient's nose is facilitated.

In accordance with one embodiment of the invention the end face of the at least one hollow body facing is angled with regard to the longitudinal axis of the hollow body. As a result, the hollow body has a greater length on one side than on the opposite side. To insert a nasal splint the longer side of the hollow body is inserted past the nasal columella into the nose of a patient. Due to the angle the hollow body does not have to be fully introduced into the nose.

In a preferred embodiment the application device has two hollow bodies, more particularly arranged in parallel to each other. The two hollow bodies can be identical. By means of such an application device two nasal splints can be introduced into both nostrils of a patient at the same time. This prevents the magnetic force of one film that is already positioned in the patient developing an undesirable effect on the film that is still to be introduced.

In one embodiment the two hollow bodies are connected to each other, wherein between the two hollow bodies an intermediate space is provided in which the columella of a patient comes to lie during an insertion procedure. An application device designed in this way can thus be introduced sufficiently far into the patient's nostrils without the columella of the patient being in the way or being stressed too much.

In one embodiment the application device comprises an operating element, more particularly a thumb rest, which is connected to both plungers and with which the plungers of both hollow bodies can be moved at the same time in both hollow bodies in one operation. In the case of this embodiment two plungers can thus be moved simply by pressing the operating element.

In accordance with the invention a nasal splint is also created which comprises a basic body made of an elastic material, wherein a nasal splint can be arranged folded together or rolled up in the hollow body of the application device. A nasal splint of this type can be of any size in relation to the nasal septum. In other words, the size of the nasal splint can be orientated to the size of the nasal septum and is not, for example, restricted by the size of a patient's nostrils.

Preferably the nasal splint has a surface area of between 1,620 and 1,750 $mm^2$, more particularly between 1,670 and 1,700 $mm^2$. This size is suitable as a standard size for various patients with differently sized nasal septa. The length of the nasal splints can be 64-70 mm, more particularly around 67. The height can be between 15 and 34 mm, whereby the nasal split has a smaller height in a frontal area than in a rear area. More particularly, the height in a frontal area can be approximately 18 mm and in a rear area approximately 31 mm.

In one embodiment the nasal splint has several magnets, more particularly NdFeB magnets, wherein the magnets are designed and arranged in such a way that the pressure of the nasal splints on the nasal septum of a patient is between 1.9 kPA and 5.6 kPA if another splint of the same type is arranged on the other side of the nasal septum. These values have also turned out to be suitable standard values for different patients with nasal septa of varying sizes. Decisive is the sum of the exerted forces in relation to the surface area on which they are acting. It has also been established that these values are the solution to the problem set out in the introduction and also result in the nasal splints being securely fixed to the nasal septum without causing local blood circulation problems or pressure necrosis.

It has been established that NdFeB magnets, for example magnets based on rare earth metals, have a high retaining force in relation to their size.

In one embodiment of the invention the basic body of the nasal splint is made of silicone, more particularly a silicone film with a silicone hardness of 30-70 Shore, preferably around 50 Shore. The basic body can thus be adapted to the shape of the nasal septum on which the nasal splint is to be applied. In the embodiment the nasal splint is sufficiently flexible to be introduced in a rolled-up state into the nose of a patient with the application device in accordance with the invention. However, at the same time the nasal splint is hard enough to distribute the pressure produced by the magnets evenly over the surface of the nasal splint to the mucous membrane and the nasal septum.

In an advantageous embodiment of the nasal splint the thickness of the basic body is thinner in marginal area than in the middle of the basic body. This prevents shear forces developing on possibly postoperatively thickened mucous membrane which could lead to injuries.

In one embodiment of the nasal splint it is produced by means of injection moulding. In contrast to production by cutting to size, production by injection moulding has the advantage that no undesirable edges or burring occur at the margins. Additionally, when produced by injection moulding the nasal splint can be made thinner in the marginal area.

More particularly, the nasal splint can be made of a film of different materials. Suitable, for example, are silicone and polyethylene, which both have a very smooth surface. The magnets can be attached to the film with acrylate adhesives.

There are various possibilities of securing the magnets on the film. In one embodiment the magnets are adhered in recesses of the carrier film. In another embodiment the magnets are covered with thin second film. In a further embodiment the magnets are baked into the film while the film is being produced.

The contour of the nasal splint is adapted to the contour of the patient's nasal septum. More particularly, the contour of the nasal splint is adapted in sections to the corresponding regions of the nasal septum so that clear allocation of the sections of the nasal splint to the corresponding areas of the nasal septum is possible.

In accordance with the invention a nasal splint device is also created comprising a nasal splint with a basic body made of elastic material and a retaining device for the detachable holding of the nasal splint in a rolled-up or folded together state. Thereby, in comparison with nasal splints in accordance with the prior art which have to be inserted into the nose in the conventional manner, the nasal splint in accordance with the invention can have a large surface area.

The retaining device can be formed by one or more loosenable threads or a retaining film which can be loosened or detached or is made of a water-soluble material, or retaining film with a perforation. Such a retaining device favours gentle introduction of the nasal splint into the patient's nose.

In an alternative embodiment the retaining device is formed by an elastic tube in which the nasal splint is arranged, wherein the nasal splint can be introduced from the elastic tube into the patient's nose by means, for example, of a plunger or by compressed air. A retaining device of his type is inexpensive to produce and simple to use.

In one embodiment complementary projections and recesses are arranged on opposite edges of the nasal splint which in the rolled-up state of the nasal splint engage which each other and can be fixed to each other by the retaining device. The retaining device can be formed by a thread or wire which is arranged within a hole in the projections. This embodiment allows simple loosening of the retaining device in order to unroll the nasal splint.

In accordance with the invention a device set is also created comprising an application device with a nasal splint accommodated in a rolled up or folded together manner in the hollow body. By means of such device the aforementioned advantages can be implemented.

In accordance with the invention a method of producing a nasal splint is also created wherein the nasal splint has a basic body with at least one recess, each for receiving at least one magnet, the method comprising the arrangement of a non-ferromagnetic body with at least one auxiliary magnet on the basic body in such a way that the auxiliary magnet exerts a magnetic attraction force on a magnet accommodated or to be accommodated in the recess; and the application, more particularly the adhesion, of a cover film on the basic body over the magnet in the recess. By means of this method it can be prevented that the holding magnets loosen from the basic body during the production of the nasal splints, more particularly because of the magnetic forces acting between the holding magnets.

In an expedient embodiment the at least one auxiliary magnet is an electromagnet so that the magnetic force can be activated during the production process and then deactivated again.

Examples of embodiments of the invention will be described in more detail below by way of the drawings. Schematically:

Figure 10:
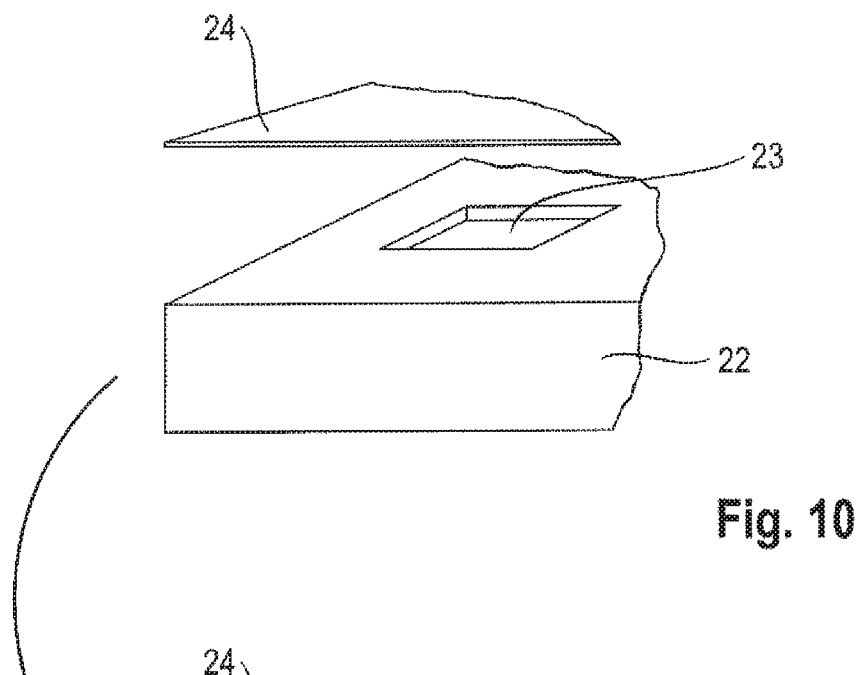
Figure 11:
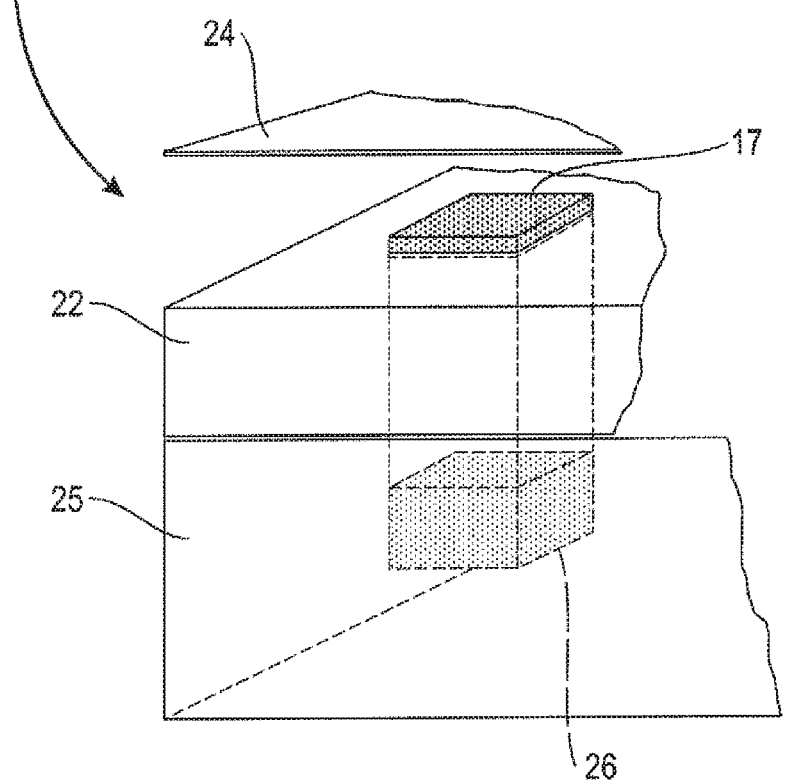

FIGS. 10 and 11 show stages in a method of producing a nasal splint 5 in accordance with one embodiment of the invention; and FIGS. 12 and 13 show a nasal splint in a further embodiment of the invention.

Figure 1:
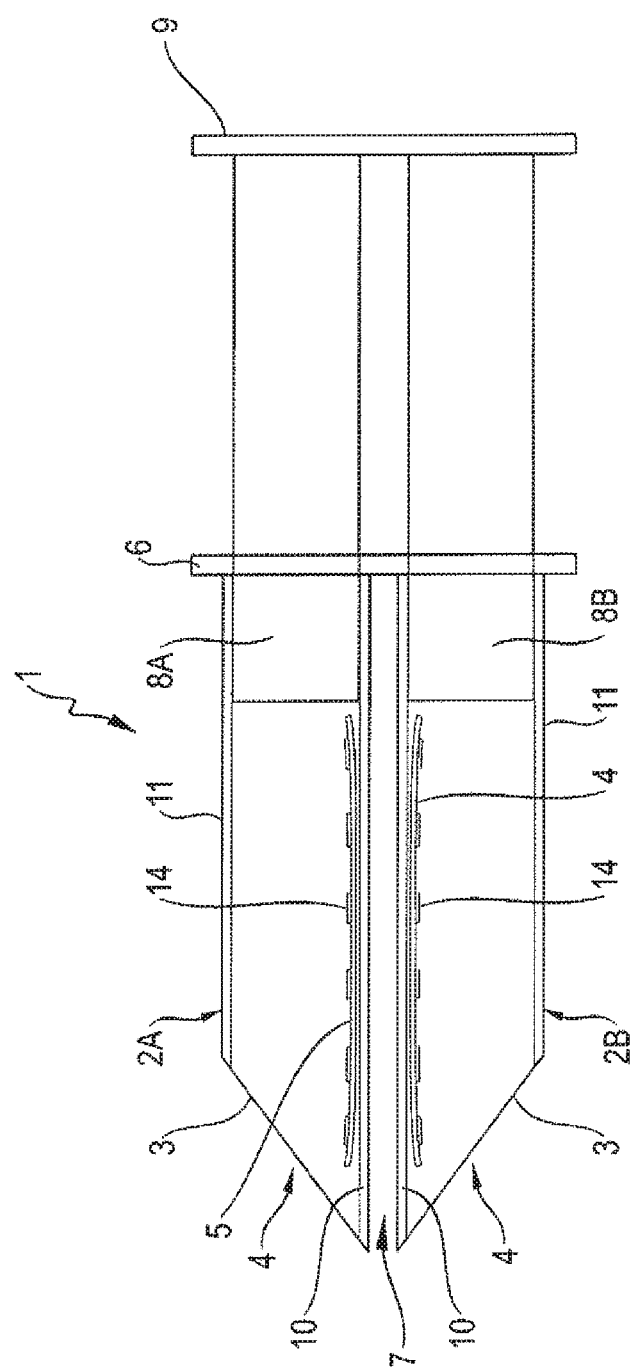
FIG. 1 shows an application device for nasal splints in accordance with one embodiment of the present invention.

FIG. 1 shows an application device 1 for nasal splints in accordance with one embodiment of the present invention. The application device comprise a first hollow body 2A and a second hollow body 2B which are essentially arranged in parallel to one another. One end face 3 of the hollow body 2A, 2B facing the patient is open (opening 4) so that nasal splints 5 accommodated in the hollow bodies can be introduced into the nose of a patient through the opening 4. The opening 4 essentially extends over the entire end face 3 of the hollow bodies 2A, 2B.

At the ends facing away from the patient the two hollow bodies 2A, 2B are connected to each other by means of a strip 6. The two hollow bodies 2A, 2B are also at a distance from each other so that between then an intermediate space 7 with an end open towards the patient is formed. The width of the intermediate space, i.e. the distance between the hollow bodies 2A, 2B essentially corresponds to the width of the columella of an average patient. For example, the distance can be between 2 and 10 mm, more particularly approximately 5-7 mm.

Arranged in each of the hollow bodies 2A, 2B is a stamp or plunger 8A and 8B respectively that is movable in the longitudinal direction. In FIG. 1 the plungers 8A, 8B are retracted so that there is space available in the hollow bodies 2A, 2B for accommodating the nasal splints 5.

At the end facing away from the patient the plungers 8A, 8B are connected to each other via a strip through which a joint thumb rest 9 is formed. Thus, through pressing the thumb rest 9 the pistons 8A, 8B can be jointly moved in the direction of the end of the application device 1 facing the patient.

The face end 3 of the hollow bodies 2A, 2B runs obliquely to the longitudinal axis of the hollowing bodies 2A, 2B. The angle between the end face 3 and the longitudinal axis of the hollow bodies 2A, 2B is in the range between 30° and 60°, preferably around 45°. As a result of this the hollow bodies each have a longer outer side 10 and a shorter outer side 11, wherein the longer outer sides 10 are on the inside, i.e. they form the intermediate space 7 between the hollow bodies 2A, 2B.

Arranged in each of the hollow bodies 2A, 2B is a rolled-up or folded together nasal splint 5. In use, the application device 1 is used to introduce the splints 5 from the hollow bodies 2A, 2B into the nose of a patient. For this the hollow bodies 2A, 2B are initially partially inserted into the patient's nostrils, whereby the columella of the patient comes to rest in the intermediate space 7 between hollow bodies 2A, 2B. By pressing on the thumb rest 9 the plungers 8A, 8B are then moved in the direction of the end of the application device 1 facing the patient so that the nasal splints 5 are pushed by the pistons 8A, 8B through the openings 4 and into the nostrils. During this the hitherto rolled-up nasal splint 5 can unroll or unfold and apply themselves to the patient's nasal septum. As will be explained below, the nasal splints 5 are fixed by magnetic force to the patient's nasal septum.

Figure 2:
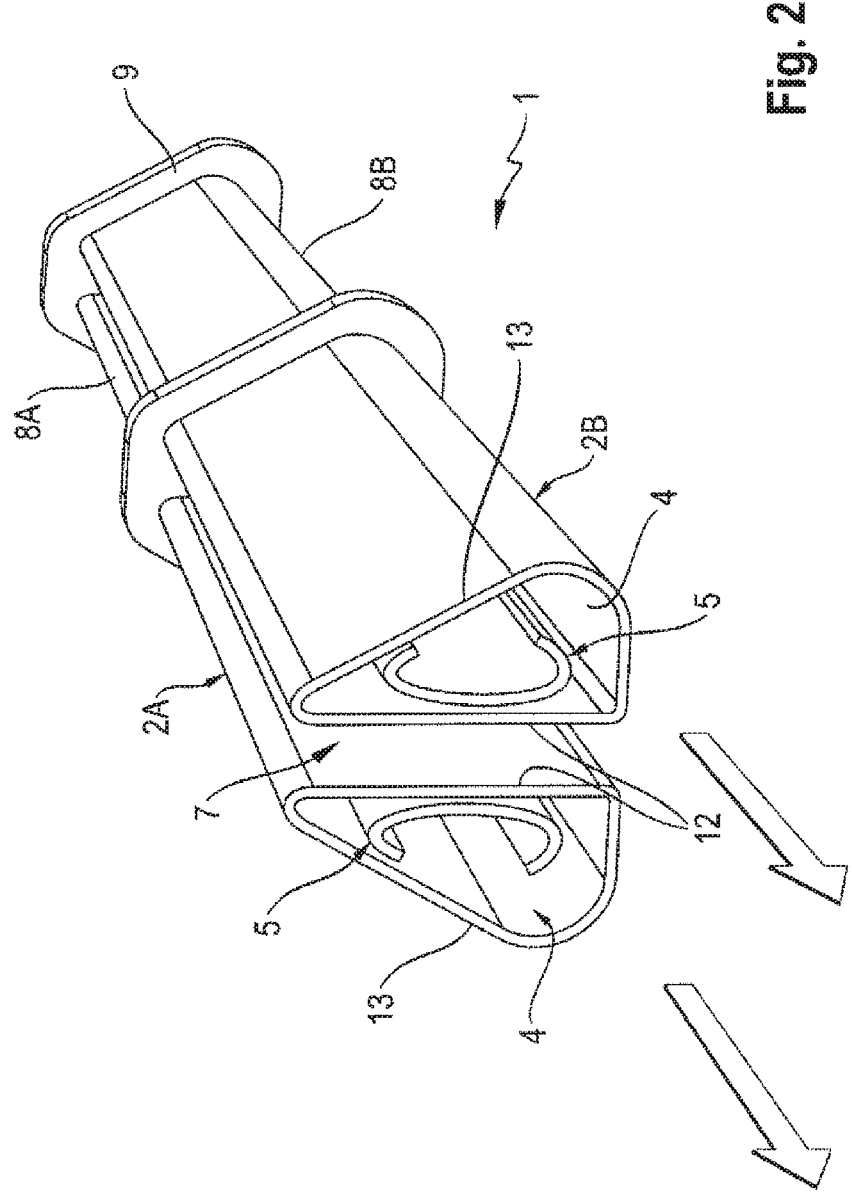
FIG. 2 shows a perspective view of the application device in FIG. 1.

FIG. 2 schematically shows a perspective view of the application device 1 in FIG. 1. It can be seen that the hollow bodies 2A, 2B each have an unrounded cross-section. More particularly, the cross-section of the hollow bodies 2A, 2B resembles the cross-section of the nostrils of an average patient. In cross-section the hollow bodies 2A, 2B each have a straight side 12 and a rounded side 13, wherein the straight sides 12 are opposite each other and define the intermediate space 7. Essentially the cross-section of each of the hollow bodies 2A, 2B corresponds to that of a wing, wherein the straight sides 12 correspond to the underside and the rounded sides 15 to the upper sides of the wing.

The arrows schematically show the direction in which the nasal splints 5 are ejected from the hollow bodies 2A and 2B when operating the plungers 8A, 8B and introduced into the nose of a patient.

In an alternative embodiment, which is not shown, the hollow bodies 2A, 2B are cylindrical in shape with a round cross-section.

The hollow bodies 2A, 2B and the plungers 8A, 8B consist of a biocompatible material.

Figure 3:
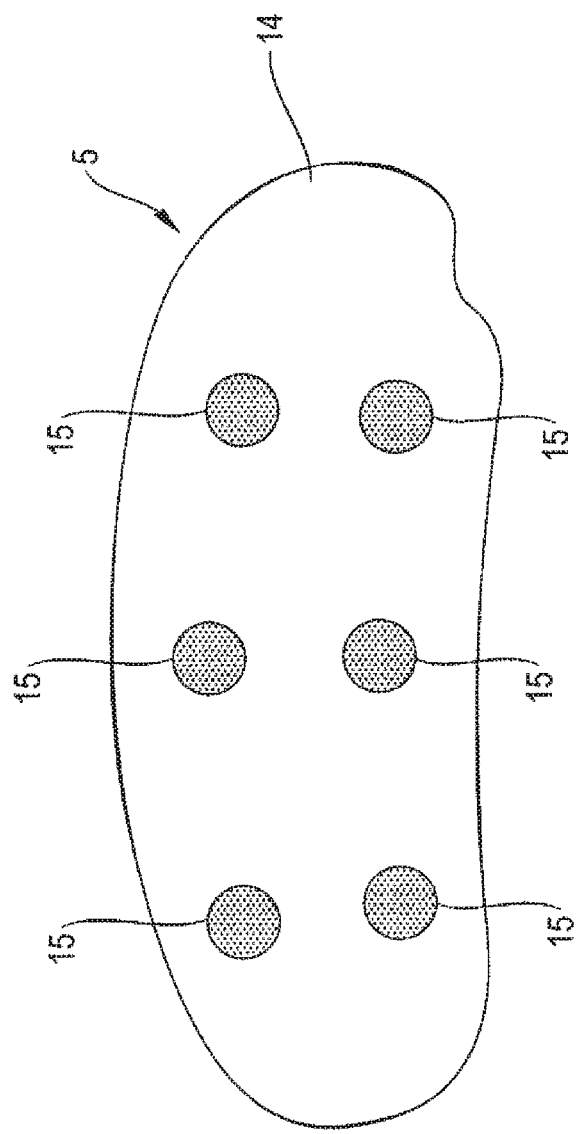
FIG. 3 shows a nasal splint in accordance with one embodiment of the invention.

FIG. 3 shows a nasal splint 5 in accordance with an embodiment of the present invention for use with the application device 1 in FIGS. 1 and 2. The nasal splint 5 has a basic body 14 made of elastic silicone. More particularly, the basic body is made of a silicone film with a silicone hardness of around 50 Shore. Through this the basic body 14 is sufficiently flexible in order to be arranged in the hollow bodies 2A, 2B of the application device in a rolled-up or folded together state, as shown schematically in FIGS. 1 and 2.

The thickness of the basic body 14 decreases in the direction towards the edge so that the contact pressure and shear forces in the marginal area the nasal splint are smaller which protects the nasal mucous membrane of the patient. Furthermore, the basic body 14 can be produced by means of injection moulding as a result of which undesirable edges or burring on the margin of the basic body 14 can be avoided.

The outer contour of the nasal splint 5 is adapted to the shape of the nasal septum of an average patient. Because of the possibility of introducing the nasal splint 5 in a rolled up state 1 into the nose of a patient by means of the application device 1 in accordance with the invention, the nasal splint 5 has a larger surface area in relation to conventional nasal splints. A standard surface area of 1685 mm$^2$ has proven to be particularly advantageous. A nasal splint 5 designed in this way can be used as standard for patients with differently sized nasal septa. There is therefore no need to individually adapt the surface area of the nasal splint depending on the patient.

In the shown embodiment the nasal splint 5 has six circular magnets 15 which are evenly distributed over the surface area of the basic body 14. By means of the magnets 15 a magnetic force is exerted on the nasal splint 5 of the same type arranged on the opposite side of the nasal septum. The magnets 15 are of such a type and arranged that the contact pressure on the nasal septum is between 1.9 kPa and 5.6 kPa.

Figure 4:
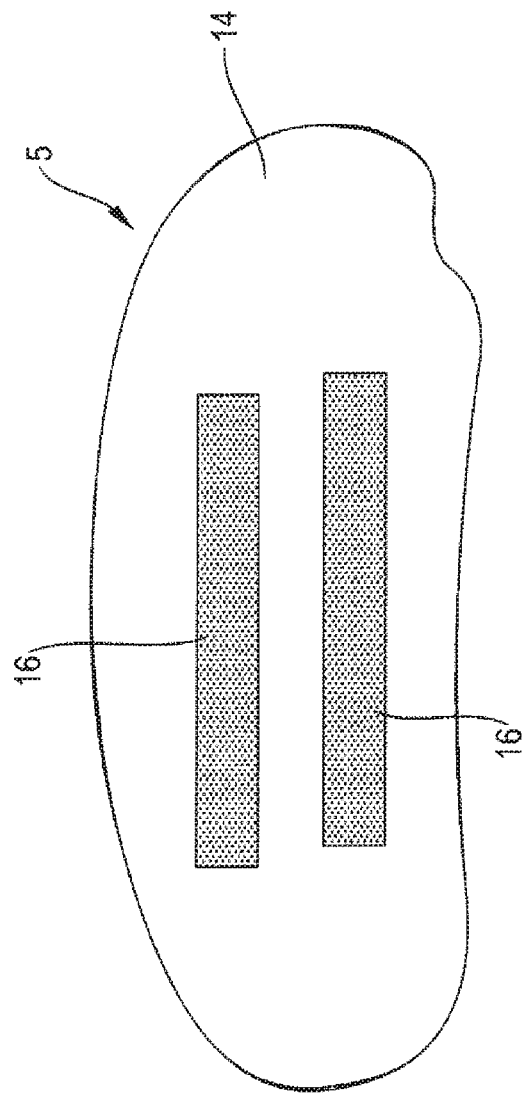
FIG. 4 shows a nasal splint in accordance with a further embodiment of the invention.

FIG. 4 shows the nasal splint 5 in an alternative embodiment. The nasal splint 5 in accordance with FIG. 4 differs from the nasal splint 5 in accordance with FIG. 3 more particularly in terms of the design and number of magnets. In the embodiment shown in FIG. 4 the nasal splint 5 has two essentially rectangular magnets 16 arranged in parallel to each other. The magnets 16 are otherwise designed so that essentially the same contact pressure is generated as through magnetics in FIG. 3. The magnetic force is determined by the material type and volumetric mass of the body. The aim of as even a contact pressure as possible can therefore be achieved more easily through a larger number of smaller magnets then through a few large magnets. The magnetic film represents a maximum manifestation of this principle.

Figure 5:
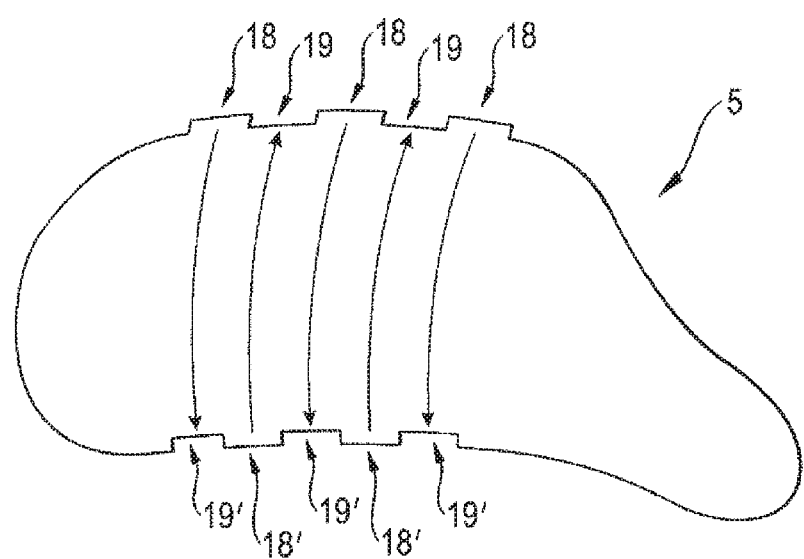
FIG. 5 shows a nasal splint in accordance with another embodiment of the invention.

FIG. 5 shows the nasal splint 5 in a further alternative embodiment of the invention. In this embodiment on one longitudinal edge the nasal splint 5 has projections 18 and adjacent recesses 19, as well as, on the opposite longitudinal edge complementary projections 18' and recesses 19'. When rolling up the nasal splint 5 the projections 18 engage in the recesses 19' and the projections 18' in the recesses 19 are shown by the arrows.

Figure 6:
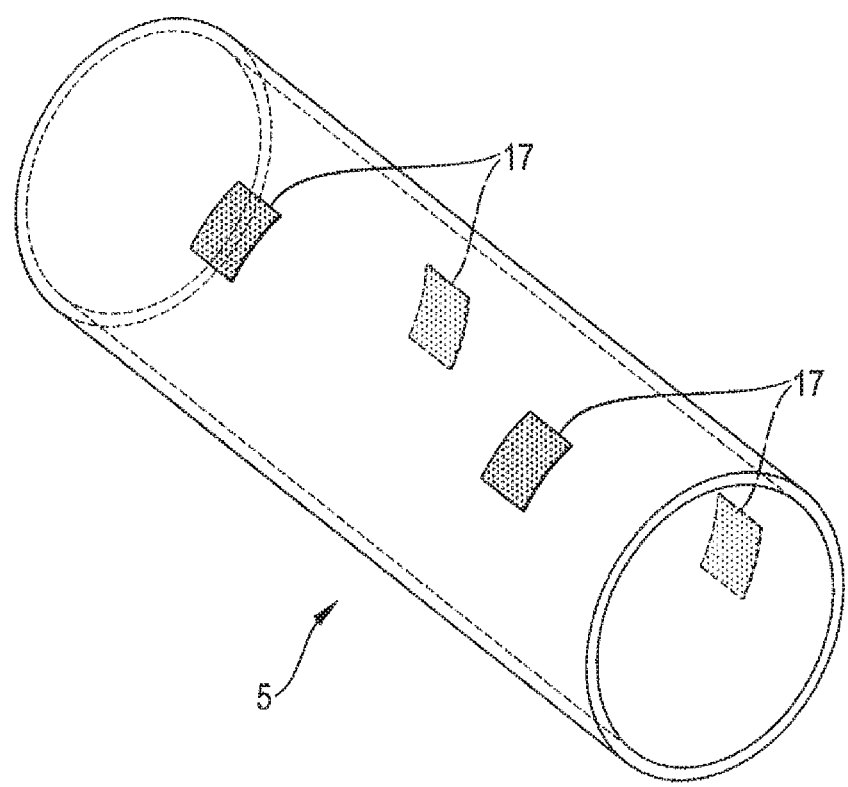
FIG. 6 shows the nasal splint in FIG. 5 in the rolled-up state.

FIG. 6 shows the nasal splint 5 from FIG. 5 in the rolled-up state with opposing magnets 17, wherein in terms of the operating principle the magnets 17 correspond to the magnet 15 and 16 in FIGS. 3 and 4.

Figure 7:
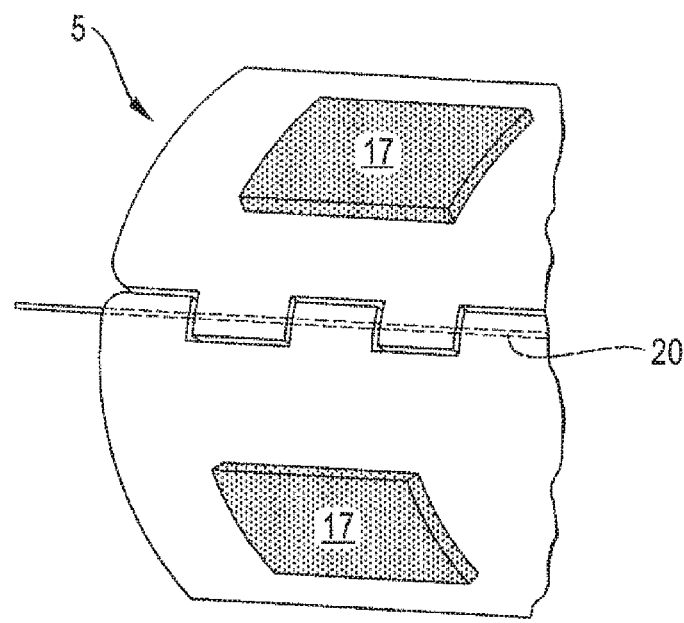
FIGS. 7 to 9 show a detailed view of the nasal splint in FIG. 5.
Figure 8:
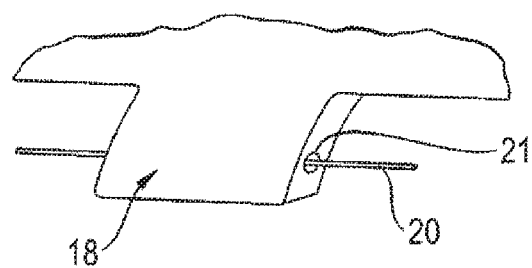
Figure 9:
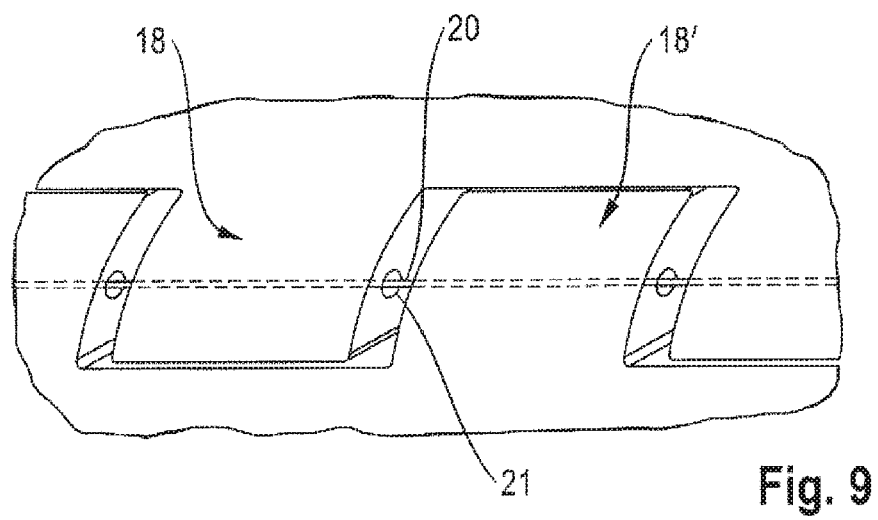

In the rolled-up state the projections 18, 18' and recesses 19, 19' engage in each other and are fixed to each other by a thread or wire as shown in detail in FIGS. 7-9. The thread 20 is arranged within a hole 21 in the projections 18, 18' extending in parallel to the outer edge of the nasal splint 18, 18'.

After introducing the nasal splint 5 into the nostril of a patient, the thread can be pulled out of the hole 21 so that the fixation is loosened and the nasal splint 5 can unroll.

FIGS. 10 and 11 show stages in a process of producing the nasal splint 5 in accordance with one embodiment of the invention. According to this, in a basic body 22 for each magnet 12 a recess 23 shaped to correspond with the magnet 17 is provided. After taking up the magnet 17 in the recess 23 a cover film 24 is adhered to the basic body 22, as a result of which the magnet 17 is fixed in the recess 23.

In order to fix the magnet 17 in its position during the production of the nasal splint 5, a non-ferromagnetic body 25 is arranged under the basic body 22. The outline of the body 25 corresponds to the basic body 22. An auxiliary magnet 26 is provided in the body 25 arranged under the recess 23 and has the opposite polarity to the magnet 17. After adhering the cover film 24 the magnet 25 can be removed again. Several such auxiliary magnets 26 can be provided, corresponding to the number of magnets 17, wherein the auxiliary magnets 26 are each arranged flush with the magnets 17.

FIGS. 12 and 13 show the nasal splint 5 in another alternative embodiment. In this embodiment a retaining film 27 is provided which holds the nasal splint 5 in the rolled up state. Along the connection point of the opposite side edges of the nasal splint the retaining film 27 has a perforation 28. By severing the retaining film 27 along the perforation 28 the nasal splint 5 can be unrolled.

In one embodiment the retaining film 27 is formed by the cover film 24 (cf. FIGS. 10 and 11).

REFERENCE NUMBERS

1 Application device
2A, 2B Hollow body
3 Face end facing the patient
4 Opening
5 Nasal splint
6 Strip
7 Intermediate space
8A, 8B Plunger
9 Thumb rest
10 Longer outer side
11 Shorter outer side
12 Straight side
13 Round side
14 Basic body
15 Round magnets
16 Rectangular magnets
17 Magnets
18, 18' Projections
19, 19' Recesses
20 Thread
21 Hole
22 Basic body
23 Recess
24 Cover film
25 Non-ferromagnetic body
26 Auxiliary magnet
27 Retaining film
28 Perforation

The invention claimed is:

1. Application device operable for the application of nasal splints, comprising at least one nasal splint, at least one hollow body for accommodating the at least one nasal splint, and a plunger which is movable inside the at least one hollow body, wherein one end face of the at least one hollow body is open so that the at least one nasal splint contained in the at least one hollow body can be introduced from the at least one hollow body through the open end face into the nose of a patient by a movement of the plunger, wherein the at least one hollow body has an at least in part unrounded cross-section.

2. Application device according to claim 1 wherein the open end face is a distal end face of the at least one hollow body which extends obliquely with regard to a longitudinal axis of the at least one hollow body.

3. Application device according to claim 1, wherein the at least one hollow body comprises first and second hollow bodies, the first hollow body having the plunger movable therein, and the second hollow body having a second plunger movable therein.

4. Application device according to claim 3 wherein the first and second hollow bodies are connected to one another and between the first and second hollow bodies an intermediate space is provided in which the columella of a patient can come to rest during an introduction procedure.

5. Application device according to claim 4, comprising a thumb rest (9) which is connected to both the plunger and the second plunger and with which the plunger and the second plunger can be moved simultaneously within the first and second hollow bodies, respectively, with one operation.

6. Application device according to claim 3 wherein the first and second hollow bodies are arranged in parallel to one another.

7. Application device according to claim 1 wherein the at least one hollow body has a cross-section with one generally straight side and an opposite, rounded, second side.

8. Application device operable for the application of nasal splints, comprising at least one nasal splint, at least one hollow body for accommodating the at least one nasal splint, and a plunger which is movable inside the at least one hollow body, wherein one end face of the at least one hollow body is open so that the at least one nasal splint contained in the at least one hollow body can be introduced from the at least one hollow body through the open end face into the nose of a patient by a movement of the plunger, wherein the open end face is a distal end face of the at least one hollow body which extends obliquely with regard to a longitudinal axis of the at least one hollow body.

9. Application device operable for the application of nasal splints, comprising first and second nasal splints, first and second hollow bodies for accommodating the first and second nasal splints, respectively, and first and second plungers which are movable inside the first and second hollow bodies, respectively, wherein a first end face of the first hollow body is open so that the first nasal splint contained in the first hollow body can be introduced from the first hollow body through the first end face into the nose of a patient by a movement of the first plunger, and, wherein a second end face of the second hollow body is open so that the second nasal splint contained in the second hollow body can be introduced from the second hollow body through the second end face into the nose of a patient by a movement of the second plunger.

10. Application device according to claim 9 wherein the first and second hollow bodies are connected to one another and between the first and second hollow bodies an intermediate space is provided in which the columella of a patient can come to rest during an introduction procedure.

11. Application device according to claim 10, comprising a thumb rest which is connected to both the first plunger and the second plunger and with which the first plunger and the second plunger can be moved simultaneously within the first and second hollow bodies, respectively, with one operation.

12. Application device according to claim 9 wherein the first and second hollow bodies are arranged in parallel to one another.

13. Application device operable for the application of nasal splints, comprising at least one nasal splint, at least one hollow body for accommodating the at least one nasal splint, and a plunger which is movable inside the at least one hollow body, wherein one end face of the at least one hollow body is open so that the at least one nasal splint contained in the at least one hollow body can be introduced from the at least one hollow body through the open end face into the nose of a patient by a movement of the plunger, wherein the at least one hollow body has a cross-section with one generally straight side and an opposite, rounded, second side.

* * * * *